(12) United States Patent
Niznick

(10) Patent No.: US 7,108,510 B2
(45) Date of Patent: Sep. 19, 2006

(54) ENDOSSEOUS DENTAL IMPLANT

(76) Inventor: Gerald A. Niznick, 3993 Howard Hughes Pkwy., #540, Las Vegas, NV (US) 89109

( * ) Notice: Subject to any disclaimer, the term of this patent is extended or adjusted under 35 U.S.C. 154(b) by 91 days.

(21) Appl. No.: 10/877,460

(22) Filed: Jun. 25, 2004

(65) Prior Publication Data

US 2005/0287496 A1 Dec. 29, 2005

(51) Int. Cl.
*A61C 8/00* (2006.01)
(52) U.S. Cl. ........................ 433/173; 433/174
(58) Field of Classification Search ................ 433/173, 433/174, 201.1
See application file for complete search history.

(56) References Cited

U.S. PATENT DOCUMENTS 4,960,381 A * 10/1990 Niznick ...................... 433/174
6,733,291 B1 * 5/2004 Hurson ....................... 433/173
2002/0110784 A1 * 8/2002 Kumar ........................ 433/173
2004/0033469 A1 * 2/2004 Blacklock ................... 433/173
2004/0033470 A1 * 2/2004 Wohrle et al. .............. 433/173
2004/0101808 A1 * 5/2004 Porter et al. ................ 433/173
2005/0233281 A1 * 10/2005 Gittleman ................... 433/173

* cited by examiner

*Primary Examiner*—Ralph A. Lewis
*Assistant Examiner*—Casey Donahoe
(74) *Attorney, Agent, or Firm*—Patrick F. Bright

(57) ABSTRACT

Endosseous dental implants include an at least partly, externally-threaded body portion, an internal cavity or shaft with an opening to the cavity or shaft at the top surface of the implant, and, in the internal cavity or shaft, a threaded portion, and a two part interlock chamber contiguous to said threaded portion including multi-lobed surfaces in a first part, and a plurality of lobes, slots or grooves in a second part.

15 Claims, 2 Drawing Sheets

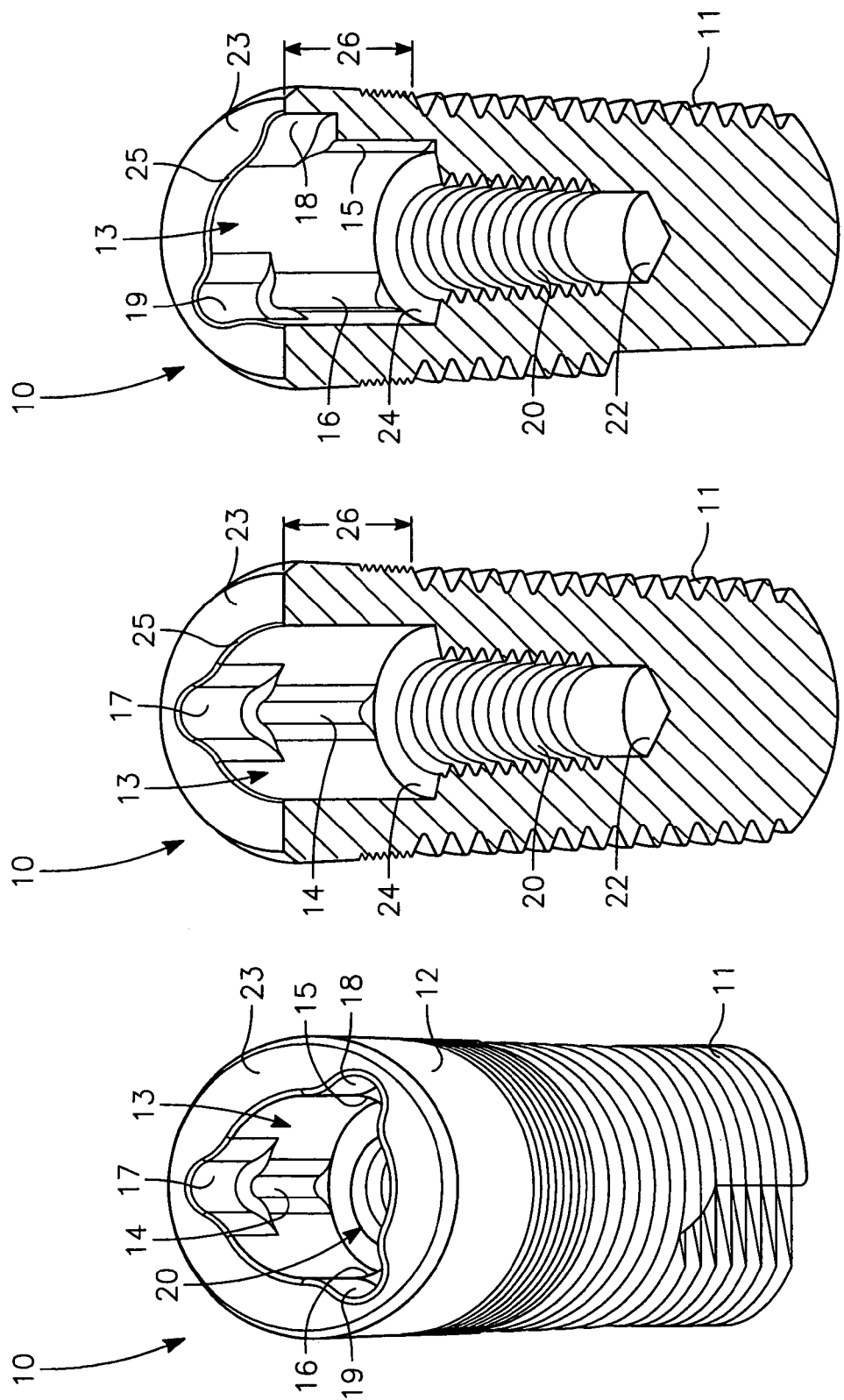

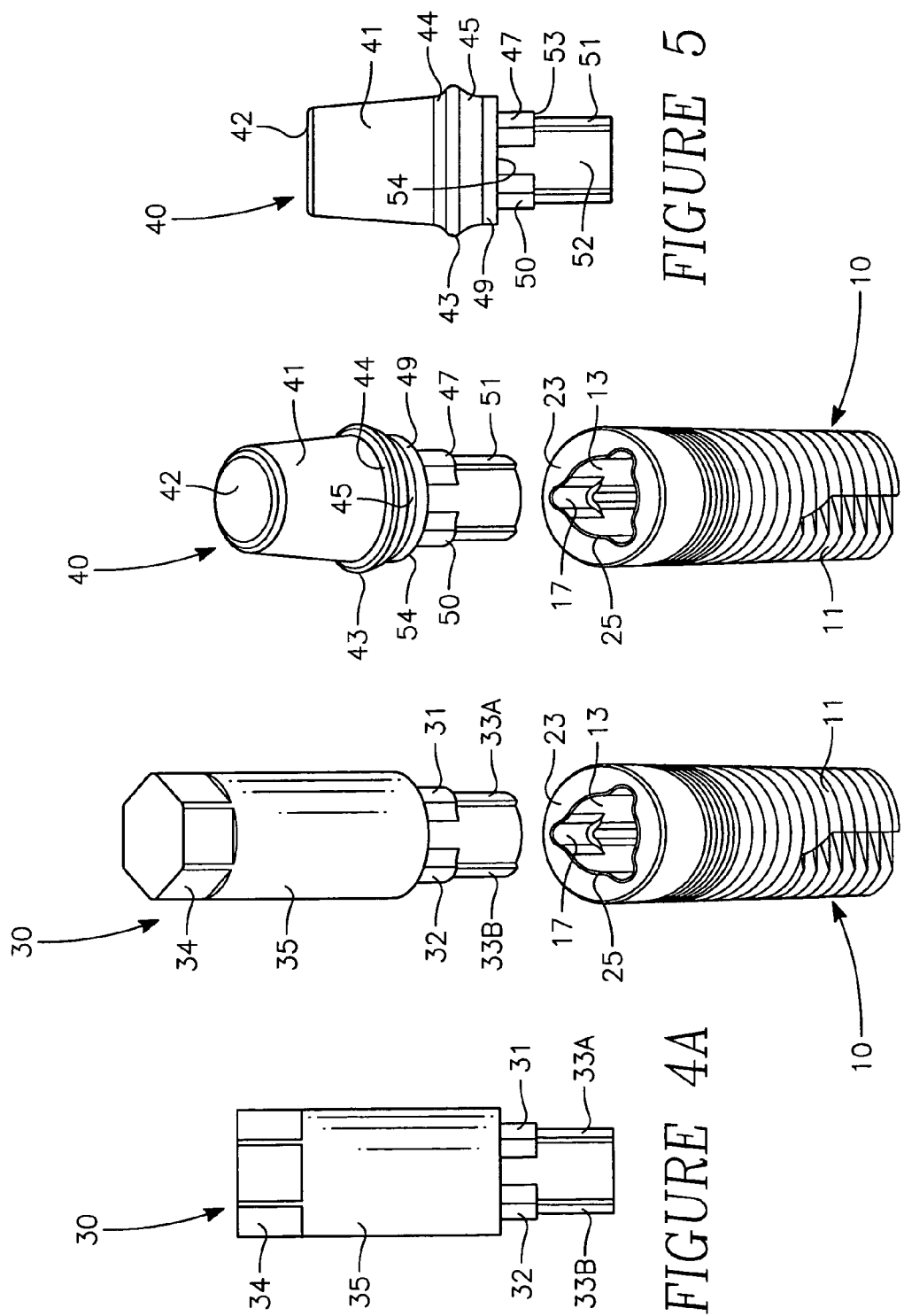

ENDOSSEOUS DENTAL IMPLANT

This invention relates to endosseous dental implants comprising an, at least partly, externally-threaded body portion, and in some embodiments, an unthreaded external top portion. These implants also comprise an internal cavity or shaft with an opening to the cavity or shaft at the top surface of the implant. This internal cavity or shaft comprises a wrench-engaging chamber, which begins in the internal cavity or shaft, at or below the top surface of the implant, and a threaded chamber extending down from the wrench-engaging chamber, and ends in the internal cavity or shaft inside the body portion. The threaded portion of the internal cavity of the implant is smaller in cross-sectional area than the wrench-engaging surfaces. The body portion may be cylindrical, conical, or tapered, and may include external, self-tapping threads on the body portion.

The wrench-engaging chamber comprises two distinct parts, namely two distinct wrench-engaging surfaces, formed in the internal cavity or shaft. A first part extends distally from a plane at or near the top surface of the implant, and includes a rounded, external profile that protrudes a first maximum radial distance from the abutment's internal sidewalls. These may be tri-lobed, and surfaces are adapted to receive and engage a complementary insertion tool for insertion of the implant into an opening or bore formed in the jawbone of a patient. A second part extends distally from one or more lobes of the first part. These protrusion(s) may have a rounded, rectangular or triangular profile, and, preferably, each protrudes a second maximum radial distance from the abutment's internal sidewalls. The second maximum radial distance is smaller than the first maximum radial distance. These protrusions are also adapted to receive and engage a complementary insertion tool.

The opening to the internal cavity or shaft of the implant may be chamfered or beveled, preferably all around the opening. The chamfered or beveled portion is, in some embodiments, of sufficient size and shape to receive and engage an abutment, adapter or other connector inserted into the opening. When the opening to the internal cavity or shaft is chamfered/beveled, a complementary adapter, connector or abutment may, in some embodiments, form a smooth, easily cleaned margin between the implant and the abutment, adapter, or connector.

The internal cavity or shaft of the dental implant is, in preferred embodiments, complementary in size and shape to abutments, adapters or other connectors, especially two-part abutments, adapters or other connectors. The abutment may be a dental component such as a healing cap, or impression post, or a temporary or more permanent abutment. In preferred embodiments, such abutments engage one or both parts of the internal wrench-engaging surfaces, and may have an inner bore that extends through the center of the abutment, with a flange or seat formed in this inner bore. Such a flange or seat supports a threaded screw which fits into and through the inner bore of the abutment, and extends beyond the inner bore for engagement with the internal threads of an implant. In preferred embodiments, these implants have a length in the range of about 8 mm to about 20 mm, and an outer diameter in the range of about 3 mm to about 7 mm. The internal cavity or shaft preferably has a length in the range of about 3 mm to about 7 mm, and a cross-section (or plurality of cross-sections) in the range of about 1.5 mm to about 3.5 mm.

BRIEF DESCRIPTION OF THE DRAWINGS

The present invention can better be understood from the following detailed description of a preferred embodiment of the invention, taken in conjunction with the accompanying drawings, in which like reference symbols refer to like parts, and in which:

FIG. 1 is a top perspective view of a preferred embodiment of an endosseous dental implant;

FIG. 2 is a cross-sectional, perspective view of the implant shown in FIG. 1;

FIG. 3 is another cross-sectional, perspective view of the implant shown in FIG. 1;

FIG. 4A is a side elevation view of an insertion tool for use with the implant of FIG. 1;

FIG. 4B is a perspective view of the insertion tool of FIG. 4A shown with the dental implant of FIG. 1;

FIG. 4C is a perspective view of an abutment of FIG. 5 shown with the dental implant of FIG. 1; and FIG. 5 is a side elevation view of the abutment of FIG. 4C.

DESCRIPTION OF THE PREFERRED EMBODIMENT

FIG. 1 shows endosseous dental implant 10 with external threading 11 over more than half the length of the external surface of implant 10, and with upper unthreaded external body portion 12. Together, external body portions 11 and 12 comprise the entire external body portion of implant 10. At the top of implant 10 is top surface 23. Below top surface 23 and internal to implant 10 is internal cavity or shaft 22. Opening 13 in top surface 23 of implant 10 leads inwardly and downwardly to internal cavity or shaft 22. Cavity 22 includes (See FIG. 2) threaded portion 20, terminating in passage 22 inside implant 10.

Starting at and extending below top surface 23, and internal to implant 10 are tri-lobed surfaces 17, 18, and 19 in interlock chamber 26. This tri-lobed surface has rounded surfaces which lie within an area that is substantially greater in size than the area within which apexes 14, 15, and 16 lie, and/or than the area occupied by the internally threaded portion 20.

Interlock chamber 26 also includes protrusions 14, 15 and 16 that extend distally from the distal ends of lobes 17, 18 and 19. Lobes 17, 18 and 19, and rounded, V-shaped or rectangular protrusions 14, 15 and 16 protrude first and second maximum radial distances into the internal walls of shaft 22. The first maximum radial distances of the tri-lobes are wider than the second maximum radial distances of the protrusions. The second maximum radial distances are all substantially the same. The tri-lobed surfaces 17, 18, and 19, and the protrusions 14, 15 and 16 are adapted to receive and engage an abutment (see FIGS. 4C, 5). The first wider tri-lobe surfaces may be denoted as insertion tool engaging surfaces. The second narrower protrusions 14, 15 and 16 may be denoted as abutment-engaging or adapter-engaging surfaces.

The external threading 11 on the external surface of implant 10 may be a multiple-lead thread, e.g. a double or triple lead thread, as described in U.S. Pat. No. 5,591,029, columns 14 and 15, or a combination of single and multiple lead threads, or quadruple and double lead threads. The text and drawings of the U.S. Pat. No. 4,960,381, issued Oct. 2, 1990, entitled "Screw-Type Dental Implant Anchor," are also incorporated by reference as though fully set forth here.

FIGS. 4B and 4C show implant 10 from a top perspective view. FIGS. 4A and 4B show a side elevation view, and a top perspective view, respectively, of an insertion tool 30 for use with implant 10. Tool 30 includes cylindrical upper body portion 35, and hexagonal or square gripping area 34 at its proximate end. At its distal end, lobe 30 includes lobes 31, 32 that fit into lobe-shaped openings 17 and 18 of implant 10. Distal cylindrical portion 33 with protrusions 33A and 33B of tool 30 extends below lobes 31 and 32, and provides additional strength and stability to tool 30. In use, tool 30 is inserted into opening 13 with lobes 31 and 32 seating in lobed-shaped spaces 18 and 17, respectively, and protrusions 33A and 33B in the slots/grooves/lobes of the second part of interlock chamber 26. A wrench, ratchet or other tool engages square or hexagonal region 34 on tool 30 to screw or otherwise turn implant 10 into place in a patient's jawbone.

FIG. 4C and FIG. 5 show side perspective view and side elevation views of abutment 40 for use with implant 10. Abutment 40 includes, at the top surface, an opening 42 and a conical and a frusto-conical shaped portion 41. Distal to portion 41 is outwardly tapering portion 44, edge 43, and inwardly, downwardly tapering sections 45 and 49. Below sections 45 and 49 are surface 54. Projecting distally from surface 54 are lobes 46, 47 and 50, each having a first maximum radial extension from outer surface 53 of abutment 40. Contiguous with and extending distally from surface 55 is rounded profile lobes 51 and 52. Lobe 51 fits into opening such as opening 55 inside implant 10 (see FIG. 4.)

Abutment 40 has an internal axially extending passage 52 through which a screw can be inserted and screwed into place in internal threads 21 inside implant 10 to hold abutment part 40 in place atop implant 10.

One advantage of the two-stage interlock chamber is that an insertion tool can, in preferred embodiments, fit into the first part with its wider lobes without engaging the second part below, permitting a dental professional to carry and insert the implant properly and precisely in an opening or bore formed in the jawbone of a patient with minimal risk of damage to the shallower lobes/grooves/slots in the second part of the interlock chamber, thereby assuring that the second stage lobes/grooves/slots provide maximum rotational stability to an abutment with corresponding protrusions.

Another advantage of the multi-lobed surfaces is that a dental professional has good tactile sense to assure full seating when inserting an abutment, adapter or connector into this surface. Furthermore, the mating, rounded surfaces of the multi-lobed abutment connection provide adequate material thickness to withstand rotational and tipping forces during mastication.

An advantage of the non-circular bevel all around, or partly around, the opening to the internal shaft, where present, is to help center the abutment, thus facilitating initial alignment of the multi-lobed surfaces. Another advantage is to provide for engagement of a mating, beveled surface on the abutment, preventing rotational movement of the abutment when fully seated in the implant and held in place by a fixation screw.

An advantage of the two-part interlock chamber is that the two distinct wrench-engaging surfaces provide greater rotational stability for abutments and greater resistance to implant deformation from insertion tools during placement of the implant into patient's jaw. The second part of the interlock chamber whether comprising rounded lobes, slots, such as rectangular slots, or V-shaped grooves, that each start at the base of the lobes in the first part of the interlock chamber and extend down to the internally threaded region, and enhance stability of abutments inserted into the implant and stability of an implant insertion tool placed into the interlock chamber.

By contrast to the implants disclosed in U.S. Pat. No. 6,733,291, the implants of this invention, and the abutment used for the implants of this invention, provide a longer, stronger interlock chamber, a stronger abutment, and a stronger abutment/implant connection. The reduced cross-section of the protrusions of the second part of the interlock chamber compared to the cross-sections of the tri-lobe first part of the interlock chamber accommodate narrowing of the diameter of tapered implant body embodiments.

The invention claimed is:

1. An endosseous dental implant comprising:
a body portion having a top surface and at least part of its external surface threaded, and an internal shaft or cavity comprising (a) an interlock chamber comprising two parts, a first part including a plurality of lobes extending distally from a plane at or near the top surface of said implant, said lobes protruding a first maximum radial distance into the internal sidewalls of said implant, and a second part extending distally from the distal end of said first part, said second part having the same number of lobes as said first part with each lobe starting at the base of a corresponding lobe in said first part, and extending a maximum radial distance into the internal sidewalls of said implant no greater than said first maximum radial distance, and having protrusions with a rounded, rectangular or triangular cross-sectional profile, and (b) an internally-threaded portion, contiguous to said interlock chamber, said internal shaft or cavity beginning at an opening in the top surface of said implant and ending inside said body portion.

2. The endosseous dental implant of claim 1 wherein said body portion is externally threaded over substantially its entire length.

3. The endosseous dental implant of claim 1 or claim 2 wherein said external surface of said body portion is partly threaded and, at or near the top of said dental implant, is unthreaded.

4. The endosseous dental implant of claim 3 wherein the body of said implant is tapered, and said second part has a maximum diameter smaller than the maximum diameter of said first part.

5. The endosseous dental implant of claim 1 or claim 2 wherein said internal shaft or cavity extends downwardly into said body portion from said opening at the top surface of said dental implant.

6. The endosseous dental implant of claim 5 wherein the body of said implant is tapered, and said second part has a maximum diameter smaller than the maximum diameter of said first part.

7. The endosseous dental implant of claim 2 wherein the body of said implant is tapered, and said second part has a maximum diameter smaller than the maximum diameter of said first part.

8. The endosseous dental implant of claim 1 further comprising a non-circular chamfer or bevel formed partly or entirely around said opening.

9. The endosseous dental implant of claim 8 wherein the body of said implant is tapered, and said second part has a maximum diameter smaller than the maximum diameter of said first part.

10. The endosseous dental implant of claim 1 further comprising a non-circular bevel or chamfer formed at the junction of the top surface of said implant and the tri-lobed surfaces.

11. The endosseous dental implant of claim 10 wherein the body of said implant is tapered, and said second part has a maximum diameter smaller than the maximum diameter of said first part.

12. The endosseous dental implant of claim 1 wherein said interlock chamber, in said first part, comprises three lobes spaced equally apart, and in said second part, comprises three lobes, slots or grooves of smaller maximum diameter than the lobes in said first part.

13. The endosseous dental implant of claim 12 wherein the body of said implant is tapered, and said second part has a maximum diameter smaller than the maximum diameter of said first part.

14. A two-piece abutment for use with the endosseous dental implant of claim 1 including a two-part interlock chamber comprising, in a first part, protrusions that can engage the lobes in the first part of said interlock chamber and in a second part, protrusions that can engage the lobes, rests or grooves in the second part of said interlock chamber.

15. The endosseous dental implant of claim 1 wherein the body of said implant is tapered, and said second part has a maximum diameter smaller than the maximum diameter of said first part.

* * * * *